US011259950B1

(12) United States Patent
Finley

(10) Patent No.: US 11,259,950 B1
(45) Date of Patent: Mar. 1, 2022

(54) LOWER LEG SUPPORT APPARATUSES AND METHODS

(71) Applicant: Ulcer Solutions, LLC, Ridgefield, WA (US)

(72) Inventor: Christopher J. Finley, Ridgefield, WA (US)

(73) Assignee: Ulcer Solutions, LLC, Ridgefield, WA (US)

( * ) Notice: Subject to any disclaimer, the term of this patent is extended or adjusted under 35 U.S.C. 154(b) by 366 days.

(21) Appl. No.: 16/276,495

(22) Filed: Feb. 14, 2019

Related U.S. Application Data

(60) Provisional application No. 62/630,723, filed on Feb. 14, 2018, provisional application No. 62/637,053, filed on Mar. 1, 2018.

(51) Int. Cl.
*A61F 5/058* (2006.01)
*A61F 5/01* (2006.01)

(52) U.S. Cl.
CPC .......... *A61F 5/0585* (2013.01); *A61F 5/0104* (2013.01)

(58) Field of Classification Search
CPC .......... A47C 20/021; A61G 13/1245; A61G 7/0755; A61G 7/075; A61F 5/0111; A61F 5/0102; A61F 5/0104; A61F 5/0585; A61F 5/0127; A61F 5/0195; A61F 5/01; A61F 13/066; A61F 5/0125; A61F 5/0113; A61F 2250/001; A61F 13/064; A61F 2/6607; A61F 5/028; A61F 5/058; A61F 13/043; A61F 13/06; A61F 2002/6614; A61F 2007/0045; A61F 5/0193; A61F 5/04; A61F 5/05; A61F 13/04; A43B 7/32; A43B 23/08; Y10S 2/911

USPC .................................................. 602/27, 23
See application file for complete search history.

(56) References Cited

U.S. PATENT DOCUMENTS

| 3,345,654 | A | | 10/1967 | Noble |
| 3,946,451 | A | * | 3/1976 | Spann ................. A61G 7/0755 5/650 |
| 4,076,022 | A | | 2/1978 | Walker |
| 4,104,746 | A | | 8/1978 | Goetz |
| 4,186,738 | A | | 2/1980 | Schleicher et al. |
| 4,573,456 | A | | 3/1986 | Spann |

(Continued)

FOREIGN PATENT DOCUMENTS

| SE | 517788 | 7/2002 |
| WO | WO 2014/154499 | 10/2014 |

*Primary Examiner* — Ophelia A Hawthorne
(74) *Attorney, Agent, or Firm* — Dascenzo Gates Intellectual Property Law, P.C.

(57) ABSTRACT

Lower leg support apparatuses can include: a member extending from a first end to a second end; opposing sidewalls of the member extending from a floor of the member above a base of the member; the sidewalls being tapered to be thicker about the first end in at least one cross section and thinner about the second end in at least another cross section; and the floor defining at least three levels of thickness in relation to the base, each of the three levels being different from any of the other levels. Methods for supporting a lower leg can include: embracing a lower leg with a support member extending between above the ankle to the mid-calf; the member providing tapered sidewalls that engage the length of the supported lower leg; and the member providing discrete support elevations that embrace the Achilles tendon, the lower leg, and the mid-calf.

20 Claims, 8 Drawing Sheets

(56) References Cited

U.S. PATENT DOCUMENTS

| | | |
|---|---|---|
| 4,616,639 A | 10/1986 | Huber |
| 5,449,339 A | 9/1995 | Drennan |
| 5,665,059 A | 9/1997 | Klearman et al. |
| 5,957,874 A | 9/1999 | Klein |
| 5,997,491 A | 12/1999 | Harris |
| 6,468,239 B1 | 10/2002 | Mollura, Sr. et al. |
| 6,572,573 B1 | 6/2003 | Klein |
| 6,793,640 B1* | 9/2004 | Avon ................ A61F 5/0111 602/23 |
| 7,188,382 B1 | 3/2007 | Taylor et al. |
| 7,458,948 B2 | 12/2008 | Drennan |
| 7,798,984 B2 | 9/2010 | Ponsi et al. |
| 7,909,787 B2 | 3/2011 | Ravikumar |
| 7,967,788 B2 | 6/2011 | Ravikumar |
| 8,070,701 B2 | 12/2011 | Flam et al. |
| 9,339,405 B2 | 5/2016 | Eriksson et al. |
| 9,392,874 B2 | 7/2016 | Shaffer |
| 9,615,958 B2 | 4/2017 | Davis et al. |
| 9,980,845 B2 | 5/2018 | Drey et al. |
| 2003/0032908 A1* | 2/2003 | Nayfa ................ A61F 5/0111 602/27 |
| 2005/0107728 A1 | 5/2005 | Vetters et al. |
| 2012/0199134 A1 | 8/2012 | Carson |
| 2013/0319426 A1* | 12/2013 | Castle .............. A61F 5/30 128/845 |
| 2015/0018740 A1 | 1/2015 | Davis et al. |
| 2018/0153729 A1 | 6/2018 | Ponsi et al. |
| 2018/0214295 A1* | 8/2018 | Davis ................ A61F 5/0113 |
| 2019/0216665 A1* | 7/2019 | Miller ............. A61G 13/1245 |

* cited by examiner

LOWER LEG SUPPORT APPARATUSES AND METHODS

CROSS REFERENCE TO RELATED APPLICATION

This application claims priority to and the benefit of U.S. Provisional Patent Application Ser. No. 62/630,723 filed Feb. 14, 2018, entitled "Heel Support Apparatus and Methods", and U.S. Provisional Patent Application Ser. No. 62/637,053 filed Mar. 1, 2018, entitled "Heel Support Apparatus and Methods", the entirety of each of which is incorporated by reference herein.

TECHNICAL FIELD

The present disclosure relates to patient care, assemblies, and methods, and in particular embodiments, lower leg support assemblies and methods.

BACKGROUND

Many patients spend long hours on bedrest during recovery from various accidents and from various forms of trauma, accidents, or illnesses. During this bedrest, patients can develop what are commonly known as bedsores. The present disclosure provides an apparatus and method for preventing, treating, and/or healing bedsores in the heel region of the patient.

SUMMARY OF THE DISCLOSURE

Lower leg support apparatuses are provided that can include: a member extending from a first end to a second end, the first end configured to engage the lower leg above the ankle and the second end configured to engage the lower leg at or below the mid calf; opposing sidewalls of the member extending from a floor of the member above a base of the member, interior portions of the sidewalls and the floor configured to embrace the lower leg; the sidewalls being tapered to be thicker about the first end of the member in at least one cross section and thinner about the second end of the member in at least another cross section; and the floor defining at least three levels of thickness in relation to the base, each of the three levels being different from any of the other three levels.

Methods for supporting a lower leg are provided. The methods can include: embracing a lower leg with a support member extending between above the ankle to the mid calf; the member providing tapered sidewalls that engage the length of the supported lower leg; and the member providing discrete support elevations that embrace the Achilles tendon, the lower leg, and the mid calf.

DRAWINGS

Embodiments of the disclosure are described below with reference to the following accompanying drawings.

DESCRIPTION

This disclosure is submitted in furtherance of the constitutional purposes of the U.S. Patent Laws "to promote the progress of science and useful arts" (Article 1, Section 8).

Figure 1:
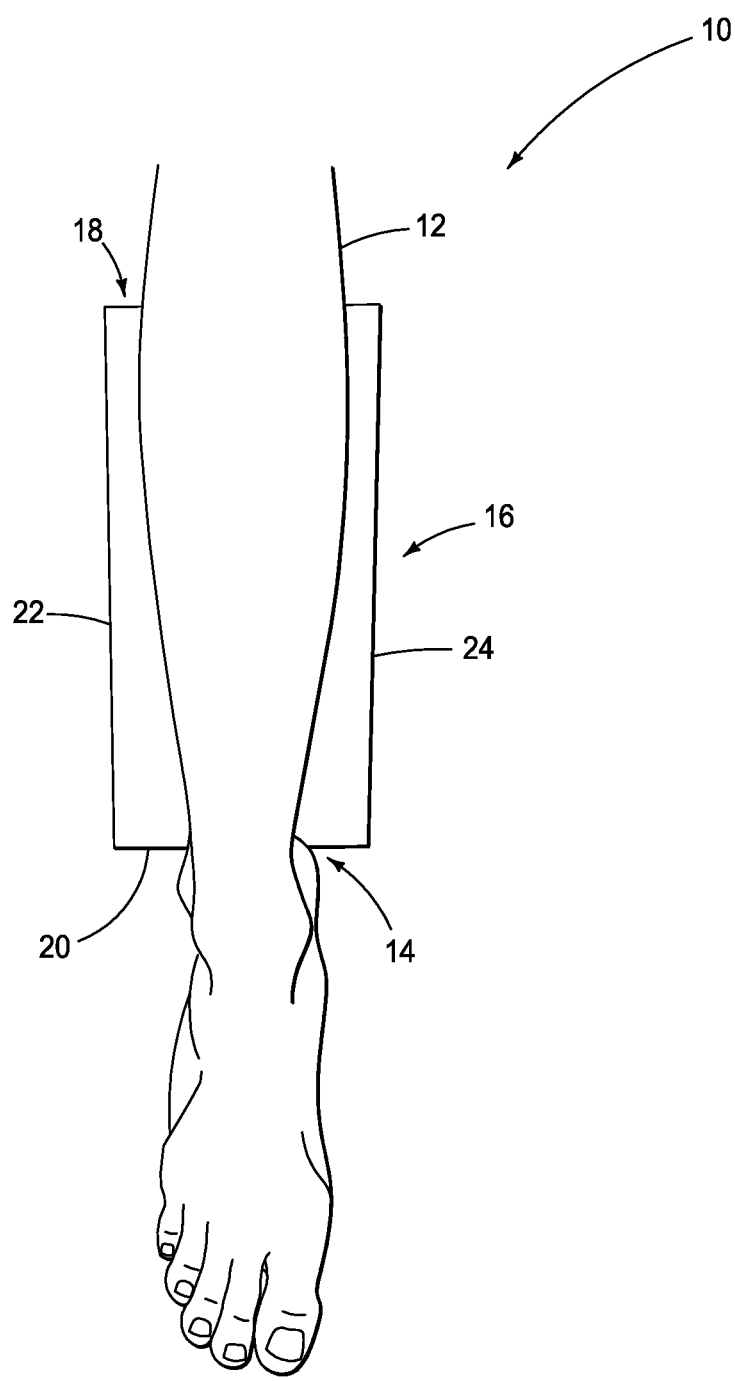
FIG. 1 is a patient appendage within a support apparatus according to an embodiment of the disclosure.

The present disclosure will be described with reference to FIGS. 1-16. Referring first to FIG. 1, a patient lower leg supported by the apparatus of the present disclosure is shown as 10. The supported patient leg is shown extending from approximately mid calf 12 toward the ankle through Achilles portion 14 with the heel free from restraint. In accordance with example embodiments, apparatus 10 can extend from the mid calf through Achilles portion 14. As can be seen, apparatus, assembly, construct, or member 16 extends through the mid calf portion to the Achilles portion 14 from end 18 to end 20. Member 16 can extend from a first end 20 to a second end 18. First end 20 can be configured to engage the lower leg above the ankle and second end 18 can be configured to engage the lower leg at or below the mid calf.

Member 16 can be constructed of a single foam or multiple foam formulations for example with different densities as desired. Open or closed celled foam may be utilized. Also, the member can be constructed of self-inflating or manual inflating air or even water bladder or bladders.

Member 16 can have opposing sidewalls 22 and 24. These sidewalls can extend from a floor 34 (see, e.g., FIG. 2) of member 16 which resides above a base 92 (see, e.g., FIG. 9). Interior portions of floor 34 and sidewalls 26 and 28 can be configured to embrace the lower leg. In accordance with at least some implementations, sidewalls can have different thicknesses from one another, from opposing sidewalls or even along a single sidewall. For example, each of the sidewalls can be tapered.

Figure 2:
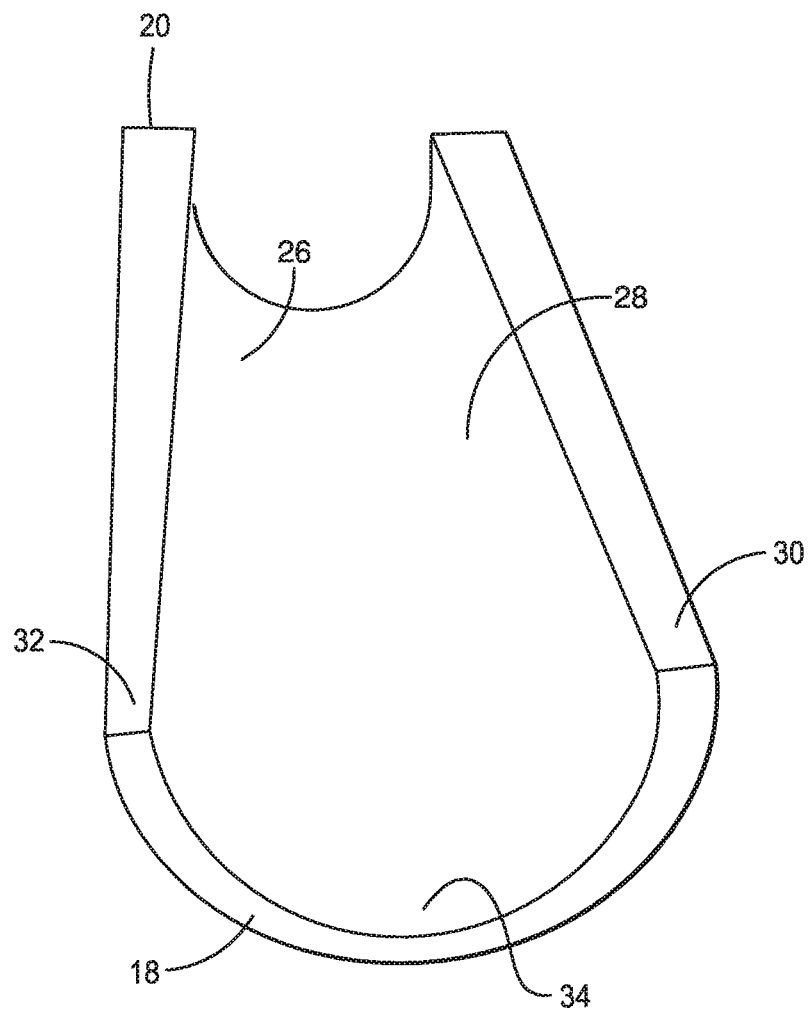
FIG. 2 is a perspective view of a support apparatus according to an embodiment of the disclosure.

Referring next to FIG. 2, member 16 can include a continuous piece that extends from end 30 through curve or floor 34 to end 32, as well as extending between opposing ends 18 and 20. As shown, the continuous piece can extend in a substantially curved fashion to form inner sidewalls 26 and 28.

Figure 3:
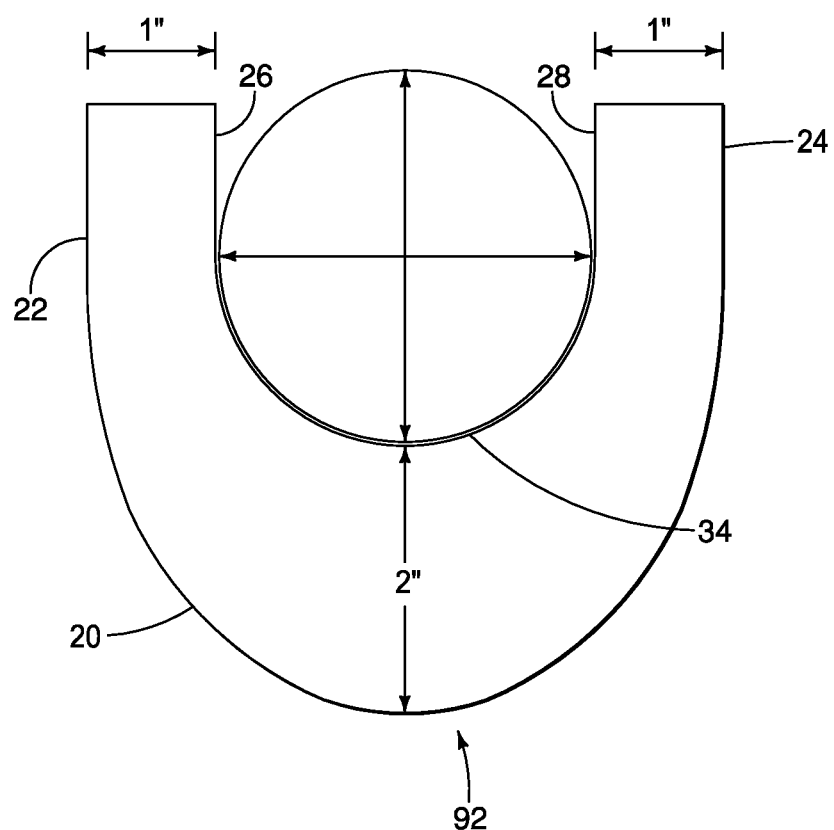
FIG. 3 is an elevational view of the support apparatus of FIG. 1 and FIG. 2 according to an embodiment of the disclosure.

Referring next to FIG. 3, as can be seen from an elevational view of end 20, the sidewalls 22 and 24 support inner portions 26 and 28 extending from floor 34 above base 92. As depicted a thickness between floor 34 and base 92 at end 20 can be about 2 inches. Additionally, this thickness can also range between 2½ and 3 inches in accordance with example implementations.

Figure 4:
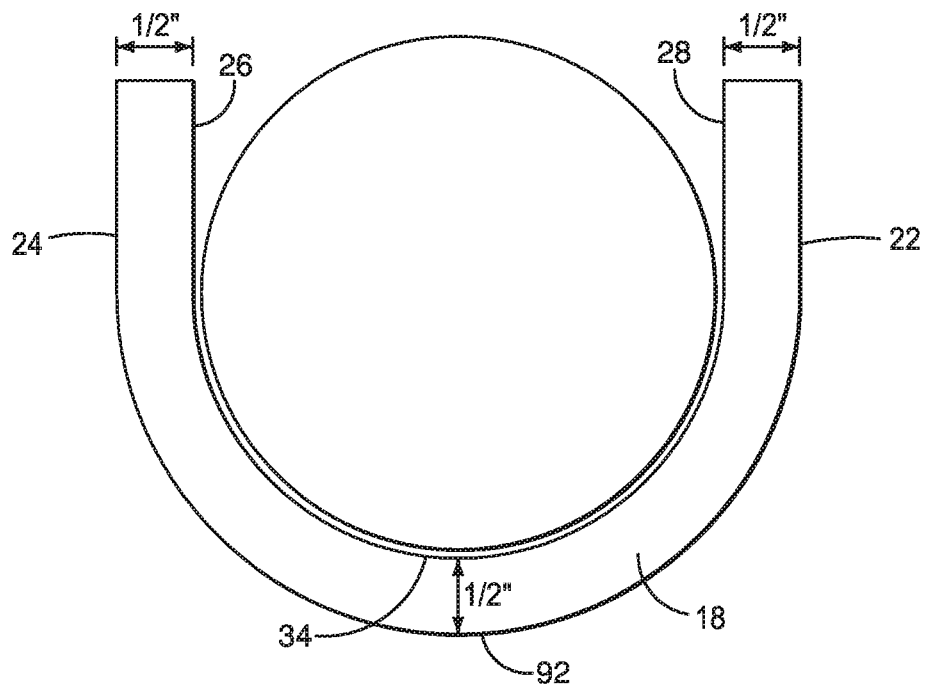
FIG. 4 is another elevational view of the support apparatus of FIG. 1, FIG. 2, and FIG. 3 according to an embodiment of the disclosure.

Referring next to FIG. 4, an elevational view of end 18 is shown having substantially similar thicknesses at sidewalls 22 and 24. However, at end 18, the thickness between base 92 and floor 34 is substantially less than the thickness at end 20. For example, this thickness at end 18 can be about ½" thick, or 25% of the thickness at end 20. This provides at least one configuration for the support to engage the lower leg below the calf and/or embrace the lower leg.

Figure 5:
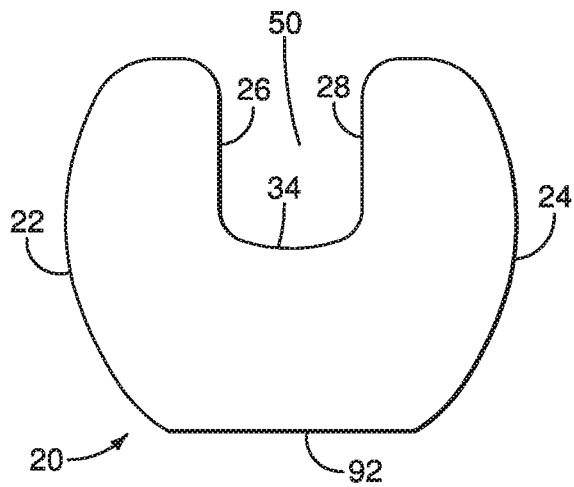
FIG. 5 is an elevational view of a support apparatus according to an embodiment of the disclosure.
Figure 6:
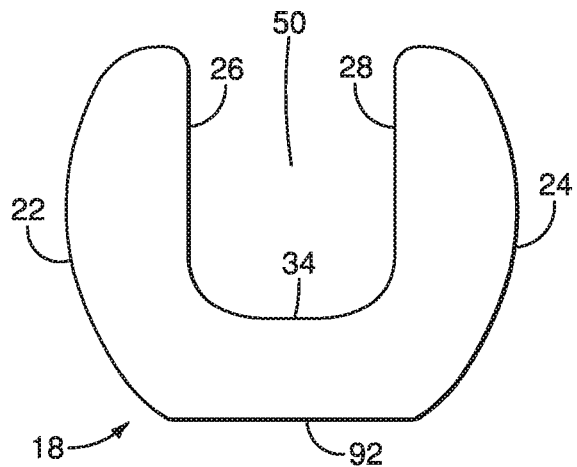
FIG. 6 is another elevational view of the support apparatus of FIG. 5 according to an embodiment of the disclosure.

Referring next to FIGS. 5 and 6, FIG. 5 represents an elevational end 20 according to another embodiment of the disclosure. As can be seen, recess 50 within the member is not curved in this embodiment but resembles a trench with curved meetings of inner sidewalls 26 and 28 with a substantially planar floor 34. Additionally, sidewalls 22 and 24 are substantially curved to meet a substantially flat base 92. Accordingly, when worn, the patient can roll the member when turning the foot or ankle so as to reach a more comfortable resting position, but also, the member can be substantially stable with the substantially flat base resting on a planar support surface such as a bed. Additionally, this substantially flat surface prevents the member from twisting about the lower leg being supported. Further, when the patient rotates the supported leg, the rounded side walls can prevent the member from twisting about the leg. As shown in FIG. 5, the thickness between base 92 and floor 34 is consistent with the thickness of end 20 described above as well as the thickness of sidewalls 22 and 24.

Referring to FIG. 6, at end 18 the trenchlike configuration of recess 50 is maintained with substantially flat floor 34 engaging inner sidewalls 26 and 28. With the thinner sidewalls and floor 34 to base 92 thickness, recess 50 is substantially larger at end 18 than end 20. Further, the curved sidewalls 22 and 24 are maintained allowing the patient to rotate the device along the lower leg axis to engage a more comfortable resting position as desired without twisting the device about the leg being supported.

Figure 7:
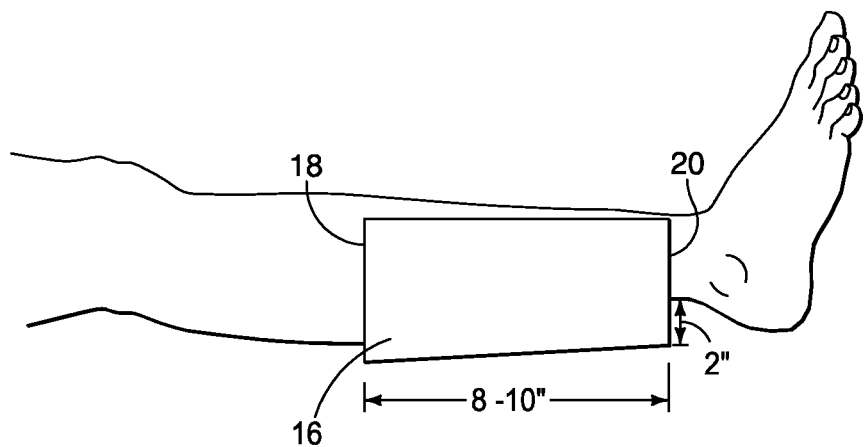
FIG. 7 is an elevational view of a support apparatus supporting a lower leg according to an embodiment of the disclosure.

Referring next to FIG. 7, apparatus 16 is shown supporting a lower leg of a patient with end 18 engaging the lower leg at or below the mid calf and end 20 engaging the lower leg above the ankle. As shown, the heel of the patient is free from engaging the surface supporting the patient.

Figure 8:
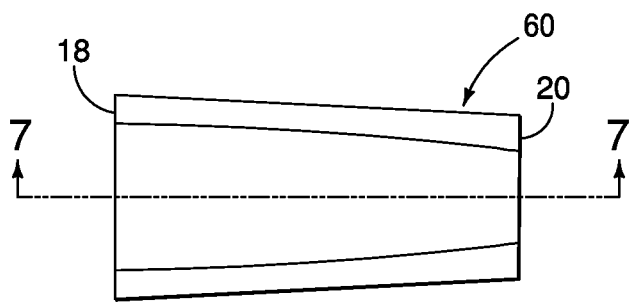
FIG. 8 is another elevational view of the support apparatus of FIG. 1, FIG. 2, and FIG. 3 according to an embodiment of the disclosure.
Figure 9:
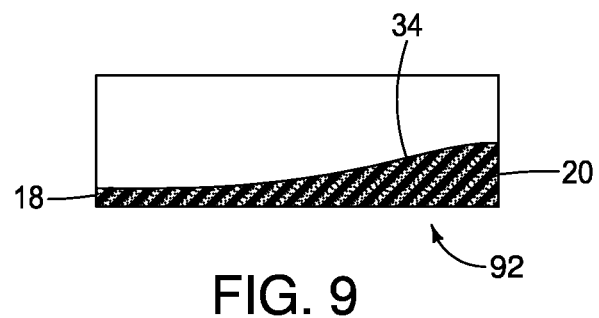
FIG. 9 is a cross section of the support apparatus of FIG. 1, FIG. 2, and FIG. 3 according to an embodiment of the disclosure.

Referring to FIGS. 8-9, at least one embodiment of apparatus 16 is shown with a top view in FIG. 8 and at least one cross section in FIG. 9. As shown, apparatus 16 at end 18 can have first thickness between a substantially flat base 92 and floor 34. At end 20, apparatus 16 can have second thickness between a substantially flat base 92 and floor 34. These thicknesses can be substantially different as shown with floor 34 changing in a non-linear fashion between end 18 and end 20. As shown floor 34 about end 18 can be configured to embrace the lower leg about the mid calf and floor 34 about end 20 can be configured to embrace the lower leg about the Achilles. Accordingly when embracing the mid calf and the Achilles, the member can provide reduced pressure on either the mid calf and/or the Achilles.

Figure 10:
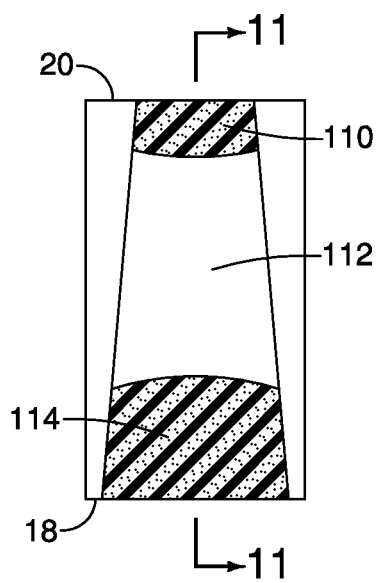
FIG. 10 is an elevational view of a support apparatus according to an embodiment of the disclosure.
Figure 11:
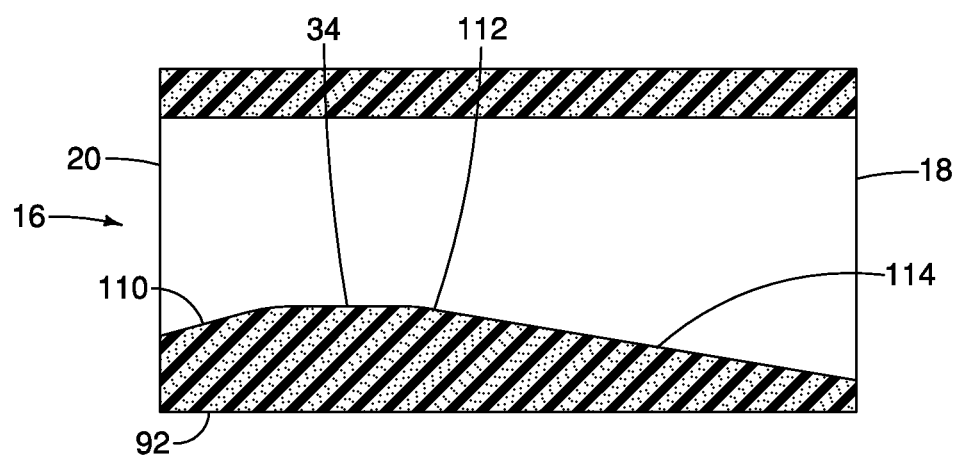
FIG. 11 is a cross section of the support apparatus of FIG. 10 according to an embodiment of the disclosure.

Referring to FIGS. 10-11, at least one embodiment of apparatus 16 is shown with a top view in FIG. 10 and at least one cross section in FIG. 11. As shown, apparatus 16 at end 18 can have first thickness between a substantially flat base 92 and floor 114. At end 20, apparatus 16 can have second thickness between a substantially flat base 92 and floor 110. Additionally, a third level of thickness can be provided between floor 112 and base 92. These three thicknesses can be substantially different as shown with floor 34 changing in a non-linear fashion between end 18 and end 20. As shown floor 114 about end 18 can be configured to embrace the lower leg about the mid calf and floor 110 about end 20 can be configured to embrace the lower leg about the Achilles. Additionally, floor 112 can have a thickness that is greater than either of the thicknesses between floor 110 and base 92 or floor 114 and base 92. Accordingly, this embodiment can define at least three levels of thickness of the floor of the member in relation to the base with each of these three levels of thickness being different from each other. In accordance with example implementations, floor 112 can support a portion of the lower leg between the mid calf and the ankle and floor 110 can provide a recess to receive the Achilles and floor 114 can provide a recess to receive the mid calf. The recesses can provide reduced pressure on the leg while being supported.

Figure 12:
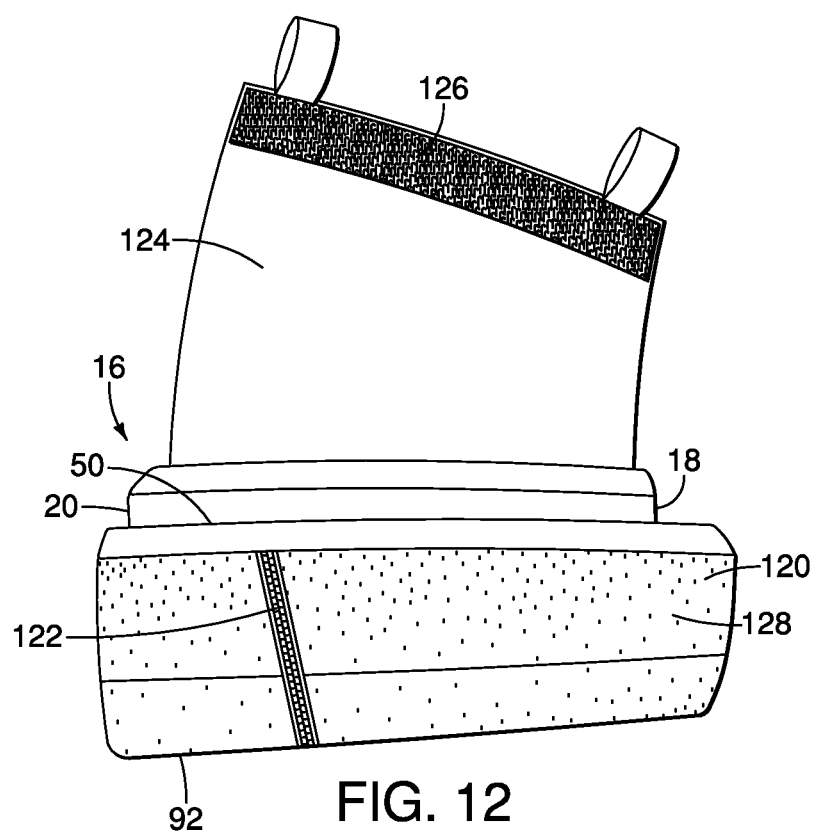
FIG. 12 is a support apparatus of the present disclosure according to another embodiment of the disclosure.
Figure 13:
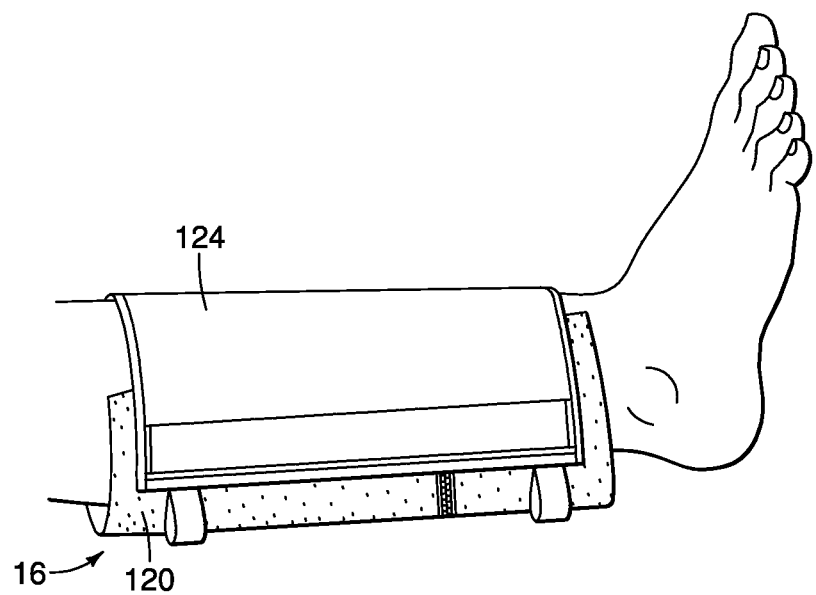
FIG. 13 is another configuration of the support apparatus of FIG. 12 according to that embodiment of the disclosure.

Referring to FIGS. 12-13, apparatus 16 is shown in accordance with another embodiment of the disclosure to include form fitting shell 120. Shell 120 can be a woven form fitting fabric that includes an opening 122 to receive the member within. This opening is configured to extend about the sidewalls and base of the member thereby removing seams or coupling devices from within recess 50 configured to embrace the lower leg. Additionally, apparatus 16 can include a cover 124 configured to extend between the sidewalls of apparatus 16. When at least partially uncoupled as shown in FIG. 12, the lower leg can be embraced by the member. When coupled via hook and loops at 126 and 128, for example, the cover can provide a biasing of the sidewalls against the lower leg to allow the member to move with the lower leg as desired.

Figures 14, 15:
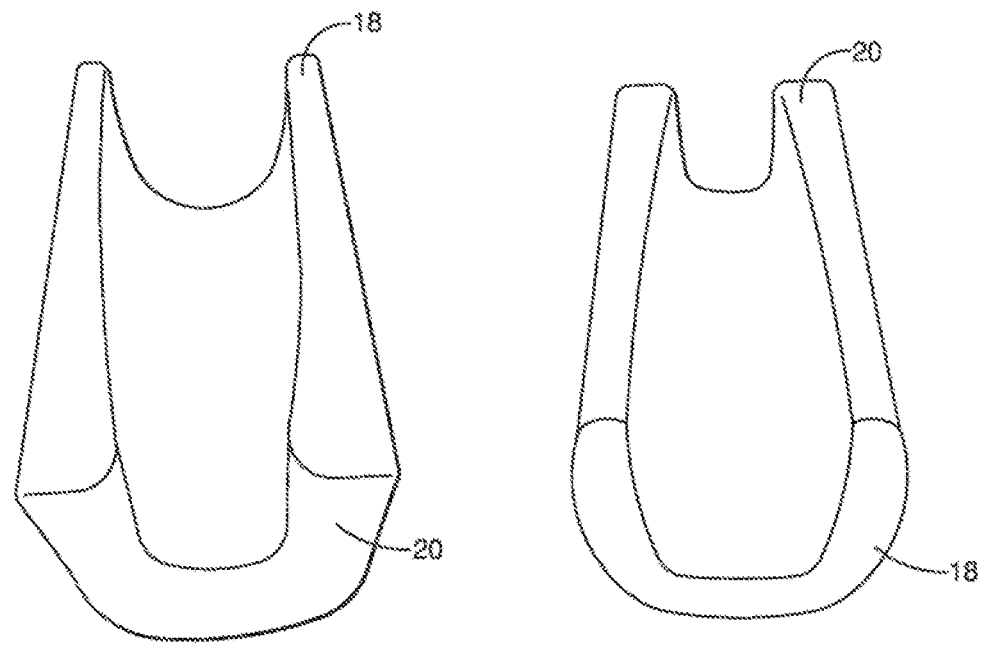
FIG. 14 is a perspective view of a portion of a support apparatus according to an embodiment of the disclosure.
FIG. 15 is another perspective view of the portion of the support apparatus of FIG. 14 according an embodiment of the disclosure.
Figure 16:
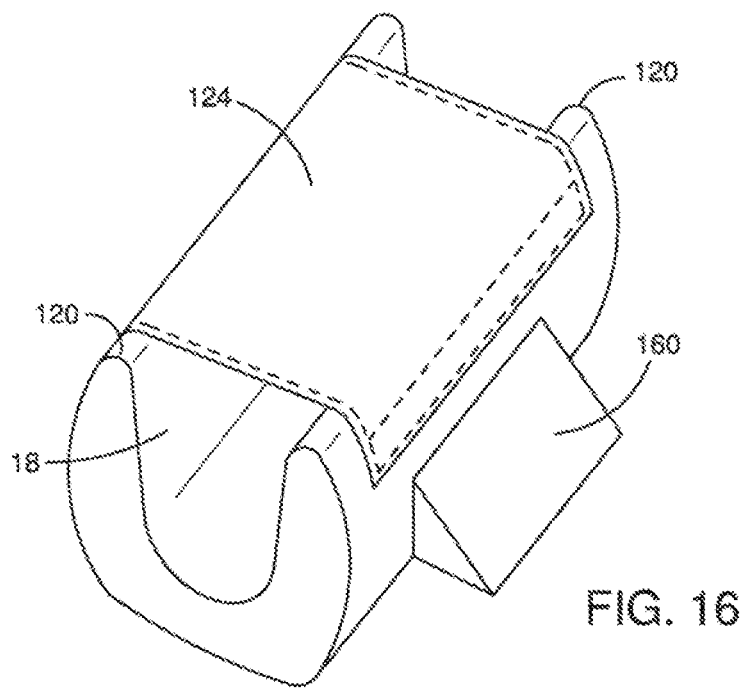
FIG. 16 is a perspective view of a support apparatus according another embodiment of the disclosure.

Referring next to FIGS. 14-15, perspective views of the member are shown. As shown the member defines a substantially U-shaped recess that is larger at end 18 than end 20. As can be seen, the sidewalls are tapered as they extend between the two ends. Additionally, and with reference to FIG. 16, a stabilizing block 160 is shown that can be reversibly coupled to a sidewall of form fitting shell 120 along a side band of hooks and loops (such as hooks and loops 126, 128 shown in FIG. 12) with block 160 having complimentary coupling devices.

In accordance with example implementations, the disclosure provides a comfortable heel off-loading device that elevates the heel from the bed and when configured as a sleeve that fits over the lower leg can remain with the patient when ambulatory to cradle the calf and lift the heel when the patient is at rest. Heel pressure ulcers develop because of prolonged pressure on the heel that limits blood supply to tissue and results in tissue death and injury, ultimately leading to ulceration. Primary treatment and prevention for heel pressure ulcers is removing pressure from the heel. This is accomplished by off-loading or floating the heel.

The current therapeutic options include several types of foam heel elevating boot apparatuses and other products designed to float the heel over the mattress (usually a pillow or foam wedge). The biggest challenge associated with off-loading the heel is patient non-compliance. The foam boot devices are bulky, uncomfortable, limit mobility both in bed and when ambulatory, and are difficult to walk in. Foam boot devices may increase the risk of falling, causing patient compliance to be low.

The present disclosure provides an apparatus which floats the heel in a unique way that allows mobility and ambulation without removing the device or having to reposition the device throughout the day and night (as in the case of wedges and pillows used to float the heels). In addition, the ulcer dressings can be changed and the heel inspected without removing the device. The cushion can be in an external pocket so that the cushion is not in direct contact with the skin. The cushion or construct can be a single or double layer design that minimizes the depth and bulk of foam or air needed to lift the heel but still provides soft foam or air for calf comfort. Limiting the size of the foam cushion can minimize any impediment to ambulation as well as mobility of the legs while the patient is in bed. The inner (medial) and outer (lateral) aspect of the foam cushion are different thicknesses with the inner being thinner than the outer, but can also provide easy ambulation without increasing fall risk.

In accordance with example implementations, the apparatus can be placed on a surface such as a bed. A leg can then be positioned in the cushion cradle and the fabric is closed over the apparatus via hooks and loops (Velcro). This can facilitate application to the patient by a caregiver even when the patient is immobile and/or unable to move the leg. The fabric can be adjusted to correct fit, accommodating various sizes of legs.

The apparatus can be used on either a left or right leg and can have a different colored thread on the seam indicating size (small, medium, large, or extra-large). According to other embodiments, the apparatus can be left/right limb or leg specific.

The apparatus never comes in contact with the ulcer as the sleeve is worn over the primary and secondary dressing and is worn over the calf and may not extend to the foot or ankle. In accordance with example implementations, the apparatus may extend above the lateral malleolus and may not extend past the heel, ankle, or foot. The apparatus is washable. The sleeve can have a rubberized (silicone) band at each end to prevent slippage on the extremity.

In compliance with the statute, embodiments of the invention have been described in language more or less specific as to structural and methodical features. It is to be understood, however, that the entire invention is not limited to the specific features and/or embodiments shown and/or described, since the disclosed embodiments comprise forms of putting the invention into effect.

The invention claimed is:

1. A lower leg support apparatus comprising:
   a member extending along a length from a first end to a second end, the first end configured to engage the lower leg above the ankle and the second end configured to engage the lower leg at or below the mid-calf;
   first and second opposing sidewalls of the member extending from a floor of the member, above a base of the member, wherein the floor is substantially flat, wherein interior portions of the sidewalls and the floor are configured to embrace the lower leg such that the heel and foot are free from restraint by the member such that the lower leg support apparatus is configured to allow inspection of the heel without removing the leg from the lower leg support apparatus, wherein the sidewalls are tapered such that the sidewalls are thicker about the first end of the member in at least one cross section and thinner about the second end of the member in at least another cross section, wherein the floor defines at least three levels of thickness in relation to the base, each of the three levels being different from any of the other three levels, wherein the base comprises a substantially flat portion, and wherein the interior portions of the sidewalls are substantially curved to meet the flat portion of the base;
   a form fitting shell comprising an opening configured to receive the member therethrough, such that the member is removably contained within the form fitting shell, and wherein the form fitting shell conforms to the member; and
   a cover extending along at least a portion of the length of the member, wherein the cover is configured to be selectively uncoupled from the form fitting shell along the first sidewall or the second sidewall to embrace the lower leg with the member, and wherein the cover is configured to bias the first and second opposing sidewalls together against the lower leg when the cover is selectively coupled to the form fitting shell along the first sidewall or the second sidewall.

2. The lower leg support apparatus of claim 1 further comprising a releasable material along the form fitting shell.

3. The lower leg support apparatus of claim 2 further comprising a stabilizing structure configured to be releasably attached to the releasable material along the form fitting shell.

4. The lower leg support apparatus of claim 1 wherein the member is comprised of a cell foam material.

5. The lower leg support apparatus of claim 1, wherein the cover extends between portions of the form fitting shell.

6. The lower leg support apparatus of claim 1 wherein the member defines a substantially U-shape in at least one cross section.

7. The lower leg support apparatus of claim 1 wherein the sidewalls are substantially pliable.

8. The lower leg support apparatus of claim 1 wherein one of the at least three levels of thickness extends from the first end of the member and another of the at least three levels of thickness extends from the second end of the member, wherein the thickness of the one level is greater than the thickness of the other level.

9. The lower leg support apparatus of claim 1 wherein the thickest of the at least three levels of thickness extends about midway between the first end and the second end of the member with the other levels of thickness bracketing the thickest level and being thinner than the thickest level.

10. The lower leg support apparatus of claim 1, wherein the base is substantially flat.

11. The lower leg support apparatus of claim 1, wherein the member is configured such that the patient can roll the member when turning the foot or ankle, so as to reach a desired resting position.

12. The lower leg support apparatus of claim 1, wherein the floor is substantially planar, and wherein the interior portions of the sidewalls have curved meetings with the floor.

13. The lower leg support apparatus of claim 1, wherein the member defines a substantially U-shape from the first end to the second end.

14. The lower leg support apparatus of claim 1, wherein the lower leg support apparatus is configured to allow patient mobility and ambulation without removing the member from the lower leg.

15. The lower leg support apparatus of claim 1, wherein the member comprises a pliable foam cushion that is configured to minimize the depth and bulk of the pliable foam such that the lower leg support apparatus is configured to lift the heel while minimizing any impediment to ambulation and mobility of the leg, and wherein the ankle is free from restraint.

16. The lower leg support apparatus of claim 1, wherein the member comprises an air bladder.

17. The lower leg support apparatus of claim 1, wherein the member comprises a water bladder.

18. The lower leg support apparatus of claim 1, wherein the member comprises a continuous piece that extends between the first and second opposing sidewalls, and through the floor of the member.

19. The lower leg support apparatus of claim 1, wherein the form fitting shell is configured to envelop the first and second opposing sidewalls and the base of the member, such that the interior portions of the sidewalls and the floor are free from seams or coupling devices.

20. The lower leg support apparatus of claim 1, wherein the member does not extend past the heel, ankle or foot.

\* \* \* \* \*